United States Patent [19]

Kauschke

[11] Patent Number: 5,513,125
[45] Date of Patent: Apr. 30, 1996

[54] PROCESS FOR DETERMINING THE PERCENTAGE OF COMBUSTIBLE GASES IN A GAS MIXTURE AS WELL AS THEIR CLASSIFICATION ACCORDING TO GAS CLASS FACTORS

[75] Inventor: Wolfgang Kauschke, Kourou, French Guiana

[73] Assignee: Drägerwerk AG, Lübeck, Germany

[21] Appl. No.: 223,442

[22] Filed: Apr. 5, 1994

[30] Foreign Application Priority Data

Apr. 8, 1993 [DE] Germany .................. 43 11 605.1

[51] Int. Cl.⁶ .................................................. G06G 7/75
[52] U.S. Cl. ...................... 364/498; 73/23.31; 73/31.01
[58] Field of Search ..................... 364/496, 497, 364/498, 499; 73/23.2, 23.21, 23.31, 31.01

[56] References Cited

U.S. PATENT DOCUMENTS

| | | | |
|---|---|---|---|
| 4,011,859 | 3/1977 | Frankenberger | 128/719 |
| 4,229,968 | 10/1980 | Muldoon | 364/497 |
| 4,266,277 | 5/1981 | Issenmann | 364/498 |
| 4,443,791 | 4/1984 | Risgin et al. | 73/23.21 |
| 4,638,443 | 1/1987 | Kaneyasu et al. | 364/497 |
| 4,670,405 | 6/1987 | Stetter et al. | 73/23.2 |
| 4,818,348 | 4/1989 | Stetter | 364/497 |
| 5,106,756 | 4/1992 | Zaromb | 364/498 |
| 5,237,539 | 8/1993 | Selman | 364/422 |
| 5,239,483 | 8/1993 | Weir | 364/497 |
| 5,265,031 | 11/1993 | Malczewski | 364/497 |
| 5,313,406 | 5/1994 | Kauppinen et al. | 364/498 |
| 5,356,819 | 10/1994 | Ritschel | 73/52.01 |

FOREIGN PATENT DOCUMENTS 466831  10/1990  France .................. G01N 27/14

Primary Examiner—Emanuel T. Voeltz
Assistant Examiner—Kyle J. Choi
Attorney, Agent, or Firm—McGlew and Tuttle

[57] ABSTRACT

In a process for determining the percentage of combustible gases in air by means of a detection element catalytically supporting the combustion, this detection element is heated with an excitation function according to a predeterminable current-voltage pattern, and the response function resulting from this is investigated with respect to the position of its maximum (differentiation). If a time interval limit (3) is exceeded by the maximum, a first gas type factor is sent to the evaluating circuit, and if the maximum does not reach the interval limit (3), a second gas type factor is determined and is evaluated as a calibrating value and for the classification of the combustible gases to be investigated.

10 Claims, 2 Drawing Sheets

PROCESS FOR DETERMINING THE PERCENTAGE OF COMBUSTIBLE GASES IN A GAS MIXTURE AS WELL AS THEIR CLASSIFICATION ACCORDING TO GAS CLASS FACTORS

FIELD OF THE INVENTION

The present invention pertains to a process for determining the percentage of combustible gases in air by means of a detection element, which catalytically supports the combustion and is incorporated in a measuring circuit, by which the detection element is cyclically heated during a heating cycle by applying a voltage according to a predeterminable current-voltage pattern (excitation function), after which the change over time in a signal value, which is supplied by the detection element and is detected by a measuring circuit, is displayed in the presence of the gas to be detected (response function), and characteristic properties occurring in the pattern of the response function are used to determine the percentage of the gas being detected by an evaluating circuit.

BACKGROUND OF THE INVENTION

Such a process has become known from EP-A 466,831. In this prior-art process, a resistor element with a catalytically active surface is exposed to the combustible gas mixture to be investigated, and the catalytic sensor is heated by a power source. The sensor is heated up during a first phase (heating phase) at constant current until a preselected resistance is reached. This resistance is maintained at a constant value during a second phase, until a steady state becomes established. The sensor remains switched off for a predetermined time during a subsequent, third phase. The voltage or the current in the steady state is used as the measured signal. Not only can the concentration of the combustible gas component in a gas mixture be determined according to the prior-art process, but information can also be provided on the type of gas over the duration of the heating phase.

However, as a rule, the determination of the duration of the heating phase is not sufficient for performing the gas measurement in a gas type-specific manner. In addition, it still remains necessary to enter a specific gas type factor into the evaluating unit when a multiple gas measuring device is to be used. The display unit of such a multiple gas measuring device is usually calibrated to one type of gas, so that the measurement of other types of gas requires a correction of this calibration value. These gas type factors are known to be calibrated to the sensitivity of methane when explosive gas mixtures are measured. The gas type factor of methane is thus set at one, so that other combustible gases have a gas type factor that is obtained from the quotient of the sensitivity of methane to the sensitivity of the gas or vapor to be investigated. As a result, a gas type factor of 1.9 is obtained for methanol, 1.5 for hydrogen, etc.

SUMMARY AND OBJECTS OF THE INVENTION

It is an object of the invention to limit the range of values of the possible gas type factors, and to improve the prior-art process such that the gas mixtures investigated can be classified from the pattern of the response function on the basis of gas class factors.

This object is attained by the excitation function showing such a function pattern that the response function passes through a maximum and that the time interval from the beginning of the rise to the time the maximum is reached is set and is compared with a time interval limit, and that, depending on the position of the time interval in relation to the interval limit, a gas class factor, by which the determination of the percentage is coupled with a classification of the gas detected, is sent to the evaluating circuit.

The advantage of the present invention is that a simple criterion is specified, with which the possible types of gas to be detected can be classified to two or more classes, each of which contains one reference gas for the determination of the gas type factor. In the first class, this is, e.g., methane, as before, with a gas type factor of 1.0, and the reference gas in the second class is methanol, whose gas type factor is also set at 1.0. Thus, all gas types which are, e.g., below the time interval limit according to the present invention, are also assigned to the class belonging to methanol, so that their gas type factors are now referred back to the new gas type factor 1.0 for methanol. The number of gas type factors is distributed between two classes or groups, so that the range of values of the gas type factors in each class is markedly reduced. The other gas type factors of the other gases falling within the same class are reduced by 1.9 by the reference gas methanol with a new gas type factor of 1, because the gas type factor for methanol was 1.9 when methanol was referred to methane, but it is now reduced to 1.0. Along with this, a higher accuracy of evaluation for the gas types falling within the class in question is achieved.

By setting the time interval limit and the position of the maximum of the response function in relation to this limit, it is possible to divide the gases to be investigated to two gas type classes: For example, exceeding the interval limit means assignment to the gas type class for which methanol is used as the reference gas with a gas type factor of 1, while the fact that the interval limit is not reached means assignment to the gas type class for which methane is used as the reference gas with a gas type factor of 1. The interval limit can be divided into smaller sections with corresponding, more finely divided time interval sections, or it can be expanded in order to divide the limits more finely and to obtain a finer division of the gas type classes.

The excitation function can be a jump function, a step function, a slope function, or a combination of these functions. A typical time interval limit for the majority of the combustible gases to be detected is between 0.1 and 10 sec.

The division into two gas type classes, one relative to methane, and the other relative to methanol, results in a list of gases of class 1, which have a gas type factor between 1.4 and 2.7, and in a list of gas types in class 2, which has a gas type factor between 1.2 and 2.0.

It is obvious that setting another time interval limit will also lead to a correspondingly different classification. Instead of methanol, it is also possible to select another gas from the set of combustible gases, which shall be used as a reference gas for determining the gas type factors. This depends essentially on the nature of the expected gas types to be detected. Besides the onset in time of the maximum of the response function, it is also possible to use the steepness of the rising slope or the number of maxima reached. The time interval limits are adjusted to it and are set accordingly.

The assignment of the gases to be investigated to two or more different gas type classes according to the criterion would also suggest that it would even be sufficient to distinguish certain types of combustible gases without immediately distinguishing the individual specific type of gas from a gas mixture.

According to a simple process for determining the type of gas, the response function is subjected to a curve analysis, and its pattern is compared with known functions, and the type of gas present is inferred from the comparison.

In an especially simple analysis of the response function, the response function is differentiated, and the differentiated response function is checked for the presence of a maximum and possibly of a minimum.

The reaching of a maximum of the differentiated response function corresponds to the beginning of the catalytic combustion at the detection element (Pellistor), and a point of extinction, at which combustion no longer takes place, is correspondingly reached when the response function is switched off, i.e., when the heating current of the Pellistor is switched off. These two properties can also be used to apply an excitation function in relation to the current-voltage pattern by means of another, individually operated detection element (i.e., without providing an additional compensator element in a bridge circuit). The point of onset (maximum) and the point of extinction (minimum), whose positions on the time axis in relation to one another are used to determine the percentage and the type of the gas, can be determined by forming the differential of the response function. A classification in terms of the pattern of the response function (number and height of the maxima, i.e., slope at the point of onset or the point of extinction of the response function) can again be performed here. On the other hand, the area under the response function between the point of onset and the point of extinction can be calculated and be related to one another with the area of the response function based on the admission of an inert calibrating gas to the Pellistor (i.e., without the presence of a combustible gas component). The simplest comparison between a combustible gas mixture and an inert calibrating gas is to form the difference of the two areas under the response functions.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

With the process of the invention, the percentage of combustible gases in air may be determined by means of a detection element catalytically supporting the combustion. The detection element is incorporated in a measuring circuit by which the detection element is cyclically heated during a heating phase and applying a voltage according to a predeterminable current-voltage pattern (excitation function). After this, the course over time of a signal value supplied by the detection element and detected by measuring circuit is represented (as noted above) in the presence of the gas to be determined. Characteristic properties appearing in the pattern of the response function are used to determine the percentage of the gas to be detected by the evaluating circuit. The excitation function is provided to have a pattern such that the response function passes through a maximum and the time interval from the start of the rise until the maximum is reached is determined and is compared with a time interval limit. Depending upon the position of the time interval in relation to the time interval limit, a gas class factor, with which the determination of the percentage is coupled with a classification of the detected gas, is sent to the evaluating circuit.

Figure 1:
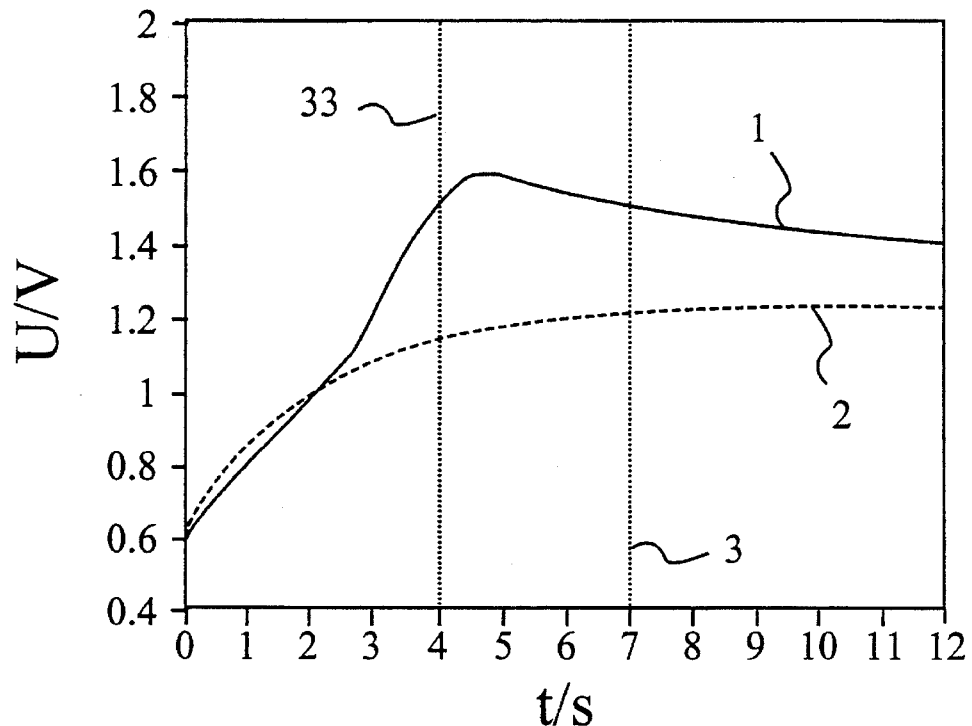
FIG. 1 is a diagram showing the response function of the voltage pattern as a function of time.

FIG. 1 shows the response function 1 for the detection of butyl alcohol at a concentration of 100% (lower explosion limit). The units for the voltage in volts are arbitrary, and the course over time covers a period of 20 sec. The excitation function, not shown, acts during this period, i.e., the current from 0 to 100 mA is switched on by the catalytically active detection element at the time T=0 and it is maintained over a period of 20 sec, and it is again switched off to 0 at the time T=20. The voltage in FIG. 1 correspondingly rises to a maximum, it becomes stabilized at a constant saturation level, and drops back to the original starting point. A response function 2 for a calibrating gas with a concentration corresponding to 0% of the lower explosion limit is represented by a broken line. At the time T=7, an interval limit 3 and an interval section 33 are represented with a dash-dotted line each, which as a distinction criterion indicates the assignment of the types of gas to be detected to classes whose maximum is located under or above this interval limit 3.

Figure 2:
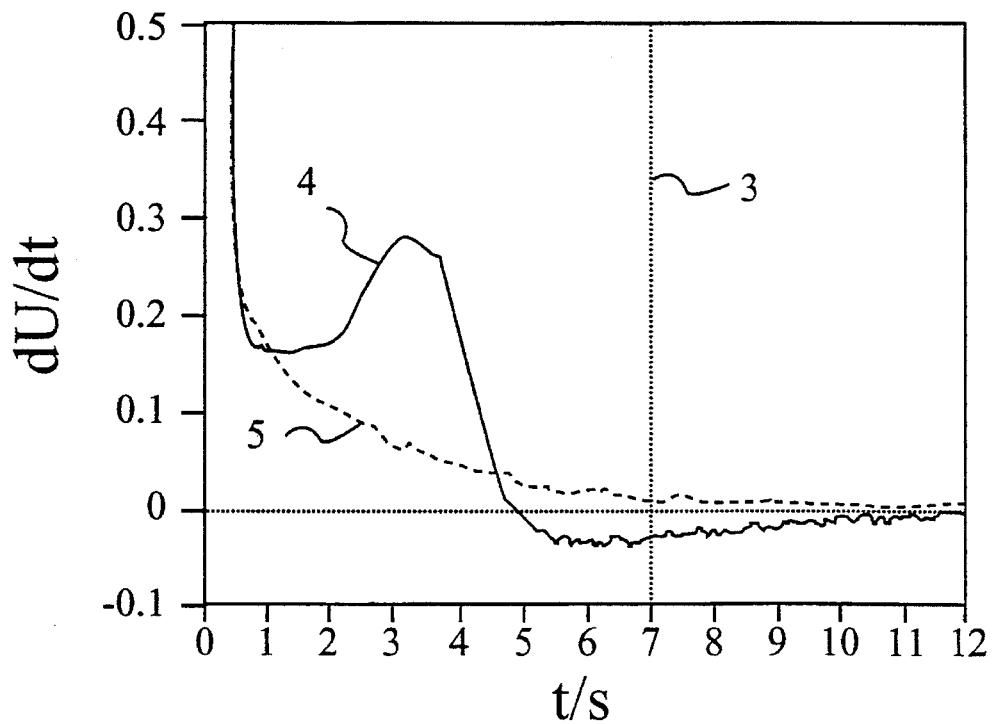
FIG. 2 is a diagram showing the differential of the response function from FIG. 1.

FIG. 2 shows the differential from the shape of the curve of the response function 1 from FIG. 1 for the assignment to the gas type classes. For the gas type butyl alcohol with a concentration of 100% of the lower explosion limit, the solid differential curve 4 is shown, whose maximum is reached at ca. 3 sec, so that it is below the interval limit 3 of 7 sec, and is consequently to be assigned to the second gas type class, whose response function maximum does not reach the interval limit 3. The differential response function 5 drawn in broken line corresponds to the response function 2 from FIG. 1.

Figure 3:
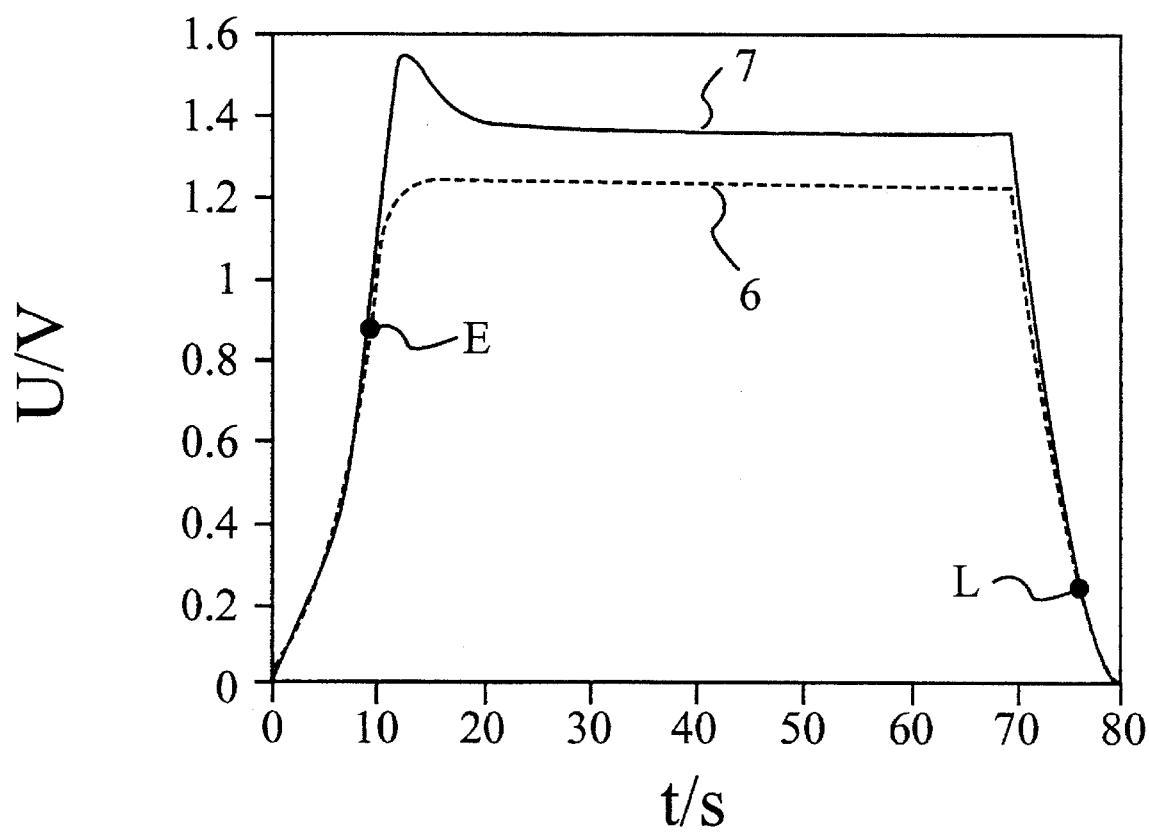
FIG. 3 is a diagram showing the response function of the current as a function of the time with the point of onset and the point of extinction.

In FIG. 3, the response function 6 of a catalytically active detection element is plotted giving the impression of a rising slope of the current over the detection element. The resulting voltage curve shows a point of onset E, at which the catalytic combustion starts and is maintained, as well as a point of extinction L, at which the catalytic combustion also stops after the current has been switched off. The response function 7 in the case of the admission of an inert calibrating gas to the catalytic detection element, i.e., without the presence of a combustible gas component, is represented by a broken line. To assign or classify the different types of gas, the area under the response function 6 is determined and is subtracted from the area under the response function 7. The remaining difference is different for each type of gas, and it can consequently be used for classification to two or more groups of gas types.

While specific embodiments of the invention have been shown and described in detail to illustrate the application of the principles of the invention, it will be understood that the invention may be embodied otherwise without departing from such principles.

What is claimed is:

1. Process for determining the percentage of combustible gases in air using a detection element catalytically supporting the combustion, the detection element being incorporated in a measuring circuit, the process comprising the steps of:

cyclically heating the detection element during a heating phase by applying a voltage according to a predeterminable current-voltage excitation function;

representing by a response function the course over a period of time a value of a signal created by the detection element and detected by the measuring circuit in the presence of the gas to be determined;

providing the excitation function with a pattern such that the response function passes through a maximum;

determining the time interval from the start of the rise of the response function until the maximum is reached;

comparing said time interval with a time interval limit; and sending a class gas factor, with which the determination of the percentage of the gas to be determined is coupled with classification of the detected gas, to the evaluation circuit;

determining the percentage of gas to be detected by an evaluating circuit using characteristic properties appearing in the pattern of the response function.

2. Process according to claim 1, wherein:

said time interval limit is divided into a plurality of time interval sections and a position of said time interval within said time interval sections defines a gas class factor.

3. Process according to claim 2, wherein:

said time interval limit and said time interval sections are set in a range from T=0.1 sec to T=10 sec.

4. Process according to claim 1, wherein:

said gas class factor includes a first gas class factor having a value such that a first class of gas types is defined with said first gas class factor, whose gas type factors are related to the gas-type factor of methane and a second gas class factor having a value such that a second class of gas types is defined with it, whose gas type factors are related to the gas type factor of methanol, which is standardized to 1.

5. Process according to claim 4, wherein:

the class of gas-type factors standardized with methane comprises the gases ethane (1.4), propane (1.8), butane (2.2), ethine (2.3), benzene (2.6), and cyclohexane (2.7); and the class of the gas-type factors standardized with methanol comprises the gases ethanol (1.2), acetone (1.3), 2-butanone (1.5), diethyl ether (1.5), ethyl acetate (1.5), n-hexane (1.5), 2-propyl alcohol (1.5), n-heptane (1.6), toluene (1.6), n-nonane (1.7), o-xylene (1.7), n-octane (1.9), and 1-butyl alcohol (2.0), wherein the decimal numbers in parentheses designate the gas type factor.

6. Process according to claim 1, wherein:

said response function is differentiated wherein the differential has at least one of a maximum and a minimum whose position on a time axis is used to determine a percentage of combustible gases and the type of gas.

7. Process for determining the percentage of combustible gases in air by means of a detection element catalytically supporting the combustion, the detection element being incorporated in a measuring circuit, the process comprising the steps of:

cyclically heating the detection element during a heating phase by applying a voltage according to a predeterminable voltage-current excitation function;

detecting a response function in the form of a course over time of a signal value supplied by the detection element in the presence of the gas to be detected;

differentiating said response function wherein the differential has at least one of a maximum and a minimum;

determining the percentage and type of the gas to be detected by an evaluating circuit using said one of said maximum and minimum appearing in the pattern of the differentiated response function whereby the excitation function is applied to the catalytically active detection element and the maximum and minimum of the curve of the differentiated response function is used to determine a percentage and the type of gas by comparison with known features of the response function.

8. Process according to claim 7, further comprising:

determining a time interval from a start of the rise of the differentiated response function until the maximum is reached;

comparing said time interval with a time interval limit to determine said type of gas.

9. Process according to claim 8, wherein:

said time interval limit is divided into a plurality of time interval sections and a position of said time interval within said time interval sections defines a gas class factor.

10. Process for determining the percentage of combustible gases in air by means of a detection element catalytically supporting the combustion, the detection element being incorporated in a measuring circuit, the process comprising the steps of:

cyclically heating the detection element during the heating phase by applying voltage according to a predeterminable current-voltage excitation function and detecting a response function in the form of the course over time of a signal value supplied by the detection element and detected by the measuring circuit, in the presence of the gas to be detected; and using properties appearing in the response function pattern to determine a percentage of gas to be detected;

determining the area under the response function;

classifying a type of the gas dependent on said area.

* * * * *